(12) United States Patent
Aurora

(10) Patent No.: US 7,910,116 B2
(45) Date of Patent: Mar. 22, 2011

(54) USE OF A BOTULINUM TOXIN TO IMPROVE GASTRIC EMPTYING AND/OR TO TREAT GERD

(75) Inventor: Sheena K. Aurora, Seattle, WA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/211,311

(22) Filed: Aug. 24, 2005

(65) Prior Publication Data

US 2007/0048334 A1 Mar. 1, 2007

(51) Int. Cl.
*A61K 39/08* (2006.01)
*A61K 39/02* (2006.01)
*A61K 39/00* (2006.01)
*A61K 38/00* (2006.01)

(52) U.S. Cl. ............... 424/247.1; 424/236.1; 424/184.1; 500/300

(58) Field of Classification Search ............... 424/184.1, 424/234.1, 236.1, 247.1; 530/300
See application file for complete search history.

(56) References Cited

U.S. PATENT DOCUMENTS

| | | | |
|---|---|---|---|
| 5,427,291 A | 6/1995 | Smith | 224/250 |
| 5,437,291 A | 8/1995 | Pasricha et al. | 128/898 |
| 5,670,484 A | 9/1997 | Binder | 514/14 |
| 5,674,205 A | 10/1997 | Pasricha et al. | 604/232 |
| 5,714,468 A * | 2/1998 | Binder | 514/14 |
| 5,756,468 A * | 5/1998 | Johnson et al. | 514/21 |
| 5,766,605 A | 6/1998 | Sanders et al. | 424/239.1 |
| 5,989,545 A | 11/1999 | Foster et al. | 424/183.1 |
| 6,063,768 A | 5/2000 | First | 514/14 |
| 6,113,915 A | 9/2000 | Aoki et al. | 424/236.1 |
| 6,139,845 A | 10/2000 | Donovan | 424/236.1 |
| 6,143,306 A | 11/2000 | Donovan | 424/236.1 |
| 6,265,379 B1 | 7/2001 | Donovan | 424/236.1 |
| 6,299,893 B1 | 10/2001 | Schwartz et al. | 424/422 |
| 6,306,403 B1 | 10/2001 | Donovan | 424/239.1 |
| 6,306,423 B1 | 10/2001 | Donovan et al. | 424/423 |
| 6,312,708 B1 | 11/2001 | Donovan | 424/423 |
| 6,328,977 B1 | 12/2001 | Donovan | 424/239.1 |
| 6,358,513 B1 | 3/2002 | Voet et al. | 424/239.1 |
| 6,358,917 B1 * | 3/2002 | Carruthers et al. | 514/2 |
| 6,365,164 B1 | 4/2002 | Schmidt | 424/239.1 |
| 6,395,277 B1 | 5/2002 | Graham | 424/184.1 |
| 6,423,319 B1 | 7/2002 | Brooks et al. | 424/239.1 |
| 6,458,365 B1 | 10/2002 | Aoki et al. | 424/239.1 |
| 6,464,986 B1 | 10/2002 | Aoki et al. | 424/239.1 |
| 6,623,742 B2 | 9/2003 | Voet | 424/236.1 |
| 6,787,517 B1 * | 9/2004 | Gil et al. | 514/1 |
| 6,838,434 B2 | 1/2005 | Voet | 514/2 |
| 2004/0037865 A1 | 2/2004 | Miller | 424/423 |
| 2004/0086531 A1 * | 5/2004 | Barron | 424/239.1 |
| 2005/0147626 A1 | 7/2005 | Blumenfeld | 424/239.1 |
| 2006/0083758 A1 | 4/2006 | Dadas | 424/239.1 |

FOREIGN PATENT DOCUMENTS

| | | |
|---|---|---|
| EP | 0 605 501 B1 | 7/1994 |
| WO | WO 95/17904 | 7/1995 |
| WO | WO2004/041303 A1 | 5/2004 |

OTHER PUBLICATIONS

Gui (Arch Pharmacol Jun. 2002, 365(Suppl 2):R22)).*
Thumshirn et al (Schweiz Rundsch Med Prax., Oct. 16, 2002;91(42):1741-7) (Abstract only).*
(Cephalagia, 2002, 22, 555-556).*
Friedenberg et al (Digestive Diseases and Sciences , vol., No. 2 Feb. 2004).*
Ahuja et al (American Family Physician, vol. 60, No. 3, Sep. 1, 1999).*
Spierings et al (Cephalalgia, 2002, 22, p. 555-556).*
Khawaja (International Journal of Dermatology 2001, 40, 311-317).*
Qureshi (Journal of Clincial Gastroenterol, 200;34(2):126-128).*
Friedenberg et al (Digestive Diseases and Sciences , vol. 49, No. 2 Feb. 2004).*
Keir, James, *Botulinum Toxin—Physiology and Applications in Head and Neck Disorders*, Neck & Head, Jun. 2005, pp. 525-535.
Lacy, Brian E., et al., *The Treatment of Diabetic Gastroparesis with Botulinum Toxin Injection of the Pylorus*, Diabetes Care, vol. 27, No. 10, Oct. 2004, pp. 2341-2347.
Miller, Larry S., et al., *Treatment of Idiopathic Gastroparesis with Injection of Botulinum Toxin into the Pyloric Sphincter Muscle*, The American Journal of Gastroenterology, vol. 97, No. 7, 2002, pp. 1653-1660.
Zhao, Xiaotuan, et al., *Botulinum Toxin for Spastic GI Disorders: A Systematic Review*, Gastrointestinal Endoscopy, vol. 57, No. 2, 2003, pp. 219-235.
Albanese A., et al., *The use of botulinum toxin on smooth muscles*, Eur J Neurol Nov. 1995; 2(Supp 3):29-33.
Bigalke H., et al., *Botulinum A Neurotoxin Inhibits Non-Cholinergic Synaptic Transmission in Mouse Spinal Cord Neurons in Culture*, Brain Research 360; 318-324:1985.
Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981.
Binz T. et al., *The Complete Sequence of Botulinum Neurotoxin Type A and Comparison with Other Clostridial Neurotoxins*, J Biological Chemistry 265(16);9153-9158:1990.
Boyd R.S. et al., *The effect of botulinum neurotoxin-B on insulin release from a β- cell line*, Mov Disord, 10(3):376:1995, Abstract 19.

(Continued)

*Primary Examiner* — Vanessa L. Ford

(74) *Attorney, Agent, or Firm* — Kenton Abel; Debra Condino

(57) ABSTRACT

Methods for treating gastric disorders, such as GERD and delayed gastric emptying, by intramuscular administration of a *botulinum* toxin to a head, neck and/or shoulder muscle of a patient with a gastric disorder.

12 Claims, 1 Drawing Sheet

OTHER PUBLICATIONS

Boyd R.S. et al., *The insulin secreting β-cell line, HIT-15, contains SNAP-25 which is a target for botulinum neurotoxin-A*, Mov Disord, 10(3):376-1995, Abstract 20.

Dykstra, D.D., et al, *Treatment of detrusor-sphincter dyssynergia with botulinum A toxin: A double-blind study*, Arch Phys Med Rehabil Jan. 1990; 71:24-6.

Eaker, E.Y., et al., *Untoward effects of esophageal botulinum toxin injection in the treatment of achalasia*, Dig Dis Sci Apr. 1997;42(4):724-7.

Gonelle-Gispert, C., et al., *SNAP-25a and -25b isoforms are both expressed in insulin-secreting cells and can function in insulin secretion*, Biochem J. 1;339 (pt 1):159-65:1999.

Gui D., et al., *Botulinum toxin injected in the gastric wall reduces body weight and food intake in rats*, Aliment Pharmacol Ther Jun. 2000;14(6):829-834.

Gui D., et al., *Effects of botulinum toxin on gastric emptying and digestive secretions. A possible tool for correction of obesity?*, Naunyn Schmiedebergs Arch Pharmacol Jun. 2002;365(Suppl 2):R22.

Habermann E., et al., *Tetanus Toxin and Botulinum A and C Neurotoxins Inhibit Noradrenaline Release From Cultured Mouse Brain*, J Neurochem 51(2);522-527:1988.

Habermann E, *Inhibition by Tetanus and Botulinum A Toxin of the release of [$^3$H]Noradrenaline and [$^3$H]GABA From Rat Brain Homogenate*, Experientia 44;224-226:1988.

Habermann, ($^{125}$I-labelled Neurotoxin from clostridium botulinum A: preparation, binding to synaptosomes and ascent to the spinal cord, Naunyn-Schmiedeberg's Arch. Pharmacol. 1974; 281, 47-56.

*Harrison's Principles of Internal Medicine* (1998), edited by Anthony Fauci et al., 14$^{th}$ edition, published by McGraw Hill.

Coffield, Eds. Jankovic J. et al., *Therapy With Botulinum Toxin*, Marcel Dekker, Inc., (1994), Chapter 1.

Kohl A., et al., Comparison of the effect of botulinum toxin A (Botox (R)) with the highly-purified neurotoxin (NT 201) in the extensor digitorum brevis muscle test, Mov Disord 2000; 15(Suppl3):165.

Kondo T., et al., *Modification of the action of pentagastrin on acid secretion by botulinum toxin*, Experientia 1977;33:750-1.

Marjama-Lyons, J., et al., *Tremor-Predominant Parkinson's Disease*, Drugs & Aging 16(4);273-278:2000.

Meyer K.E. et al, *A Comparative Systemic Toxicity Study of Neurobloc in Adult Juvenile Cynomolgus Monkeys*, Mov. Disord 15(Suppl 2);54;2000.

Moyer E et al., *Botulinum Toxin Type B: Experimental and Clinical Experience*, chapter 6, pp. 71-85 of "Therapy With Botulinum Toxin", edited by Jankovic, J. et al. (1994), Marcel Dekker, Inc.

Naumann M., et al., *Botulinum toxin type A in the treatment of focal, axillary and palmar hyperhidrosis and other hyperhidrotic conditions*, European J. Neurology 6 (Supp 4):S111-S115:1999.

Sloop, *Neurology*, 48:249-53:1997.

Pearce, L.B., *Pharmacologic Characterization of Botulinum Toxin For Basic Science and Medicine*, Toxicon 35(9);1373-1412 at 1393, 1997.

Ragona, R.M., et al., *Management of partoid sialocele with botulinum toxin*, The Laryngoscope 109:1344-1346:1999.

Rohrbach S., et al., *Botulinum toxin type A induces apoptosis in nasaal glands of guinea pigs*, Ann Otol Rhinol Laryngol Nov. 2001;110(11):1045-50.

Rohrbach S., et al., *Minimally invasive application of botulinum toxin type A in nasal hypersecretion*, J Oto-Rhino-Laryngol Nov.-Dec. 2001;63(6):382-4.

Rossi S., et al., *Immunohistochemical localization of SNAP-25 protein in the stomach of rat*, Naunyn Schmiedebergs Arch Pharmacol 2002;365(Suppl 2):R37.

Sanchez-Prieto, J., et al., *Botulinum Toxin A Blocks Glutamate Exocytosis From Guinea Pig Cerebral Cortical Synaptosomes*, Eur J. Biochem 165;675-681:1987.

Schantz E.J., et al Preparation and characterization of botulinum toxin type A for human treatment (in particular pp. 44-45), chapter 3 of Jankovic, J., et al, Therapy with Botulinum Toxin, Marcel Dekker, Inc (1994).

Schantz, E.J., et al, *Properties and use of Botulinum toxin and Other Microbial Neurotoxins in Medicine*, Microbiol Rev. 56;80-99:1992.

Singh, *Critical Aspects of Bacterial Protein Toxins*, pp. 63-84 (chapter 4) of Natural Toxins II, edited by B.R. Singh et al., Plenum Press, New York (1996).

Wang Z., et al., *Effects of botulinum toxin on gastric myoelectrical and vagal activities in dogs*, Gastroenterology Apr. 2001;120(5 Suppl 1):A-718.

Weigand et al, (*125I-labelled botulinum A neurotoxin:pharmacokinetics in cats after intramuscular injection*, Nauny-Schmiedeberg's Arch. Pharmacol. 1976;292, 161-165.

Wiesel P.H. et al., *Botulinum toxin for refractory postoperative pyloric spasm*, Endoscopy 1997;29(2):132.

\* cited by examiner

Figure 1     Locations of Muscles Injected.
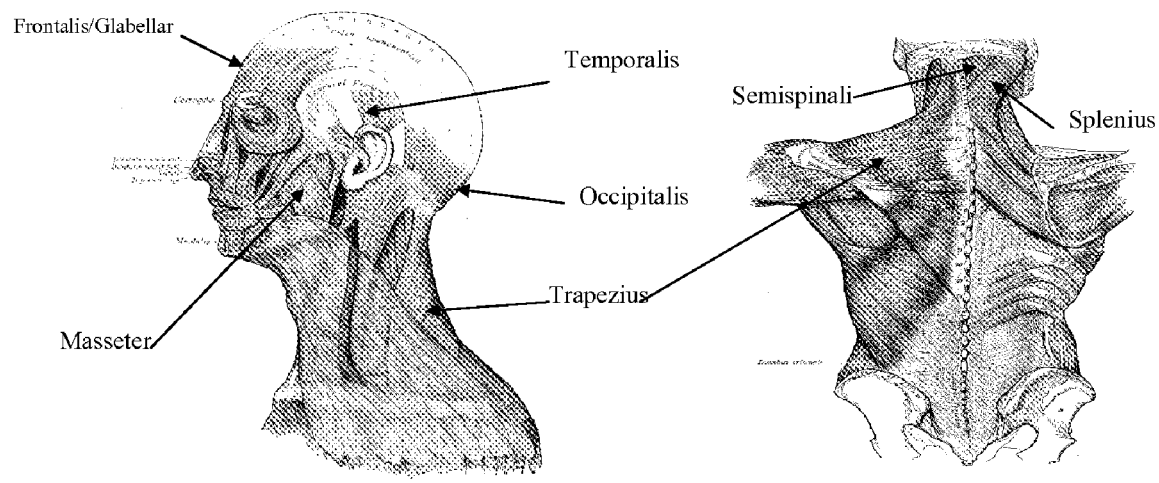

USE OF A BOTULINUM TOXIN TO IMPROVE GASTRIC EMPTYING AND/OR TO TREAT GERD

BACKGROUND

The present invention relates to methods for treating various gastric disorders, such as delayed or impeded gastric emptying and/or gastroesophageal reflux disease ("GERD"). In particular, the present invention relates to methods for treating various gastric disorders (such as Crohn's disease, diverticulosis, diverticulitis, gallstones, GERD, hiatal hernia, heartburn, gastric stasis, gastric emptying, pyloric valve (or other GI sphincter) malfunction or spasm, *H. pylori* induced ulcers, peptic ulcers, irritable bowel syndrome, stomach ulcers, duodenal ulcers, colitis and ulcerative colitis) with a *botulinum* neurotoxin.

Gastroesophageal Reflux Disease

Gastroesophageal reflux disease (GERD) (also called peptic esophagitis and reflux esophagitis) is an inflammation of the esophagus resulting from regurgitation of gastric contents into the esophagus. Some gastroesophageal reflux is a normal condition that often occurs without symptoms after meals. However, the reflux can be become more serious when it is due to an incompetent (weakened) lower esophageal sphincter, a band of muscle fibers that closes off the esophagus from the stomach. When this occurs, acidic or alkaline gastric contents from the stomach can return to the esophagus through the lower esophageal sphincter and cause the symptoms of GERD. Conditions which can cause an incompetent esophageal sphincter with resulting s GERD include pregnancy, hiatal hernia, obesity, recurrent or persistent vomiting, and nasogastric tubes. GERD is also a risk factors of esophageal surgery and esophageal stricture.

The symptoms of GERD include heartburn, belching, regurgitation of food, nausea, vomiting, hoarseness of voice, sore throat, difficulty swallowing and cough. Diagnostic of GERD is stool positive for guaiac, continuous esophageal pH monitoring showing reflux, endoscopy showing esophagitis or ulceration, esophageal manometry showing abnormal sphincter pressure, a barium swallow showing reflux, and a positive Bernstein test for gastric acid reflux Treatment for GERD measures include weight reduction, avoiding lying down after meals, sleeping with the head of the bed elevated, taking medication with plenty of water, avoiding dietary fat, chocolate, caffeine, peppermint (these can cause lower esophageal pressure), avoiding alcohol and tobacco. Medications that can alleviate symptoms of GERD include antacids after meals and at bedtime, histamine H2 receptor blockers, promotility agents, proton pump inhibitors. Furthermore, anti-reflux operations (Nissen fundoplication) may be indicated for a patient with pharmacologically intractable GERD. Untreated GERD can result in esophagitis, esophageal ulcer, bronchospasm, chronic pulmonary disease and Barrett's esophagus, the latter being a change in the lining of the esophagus that can increase the risk of cancer.

Ulcers

During normal digestion, food moves from the mouth down the esophagus into the stomach. The stomach produces hydrochloric acid and the enzyme pepsin to digest the food. From the stomach, food passes into the upper part of the small intestine, the duodenum, where digestion and nutrient absorption continue.

An ulcer is a sore or lesion that forms in the lining of the stomach or duodenum where acid and pepsin are present. Ulcers in the stomach are called gastric or stomach ulcers. Ulcers in the duodenum are called duodenal ulcers. Collectively, ulcers in the stomach and duodenum are called peptic ulcers. Ulcers rarely occur in the esophagus or in the first portion of the duodenum, the duodenal bulb.

About 20 million Americans develop at least one ulcer during their lifetime. Additionally, ulcers affect about 4 million people and more than 40,000 people have surgery each year because of persistent symptoms or problems from ulcers and tragically, about 6,000 people die each year from ulcers or ulcer related complications.

Ulcers can develop at any age, but they are rare among teenagers and even more uncommon in children. Duodenal ulcers occur for the first time usually between the ages of 30 and 50. Stomach ulcers are more likely to develop in people over age 60. Duodenal ulcers occur more frequently in men than women, while stomach ulcers develop more often in women than men.

It is believed that three factors, lifestyle, acid and pepsin, and the bacterium *Helicobacter pylori* play a role in ulcer development. Thus, lifestyle factors such as stress and diet can contribute to ulcer formations. Additionally, an imbalance between digestive fluids (hydrochloric acid and pepsin) and the stomach's ability to defend itself against these powerful substances can result in ulcers. Finally, an ulcer can develop as a result of infection with the *H. pylori*.

The stomach's inability to defend itself against the powerful digestive fluids, acid and pepsin, contributes to ulcer formation. Thus, excessive digestive fluids, acid and/or pepsin present in the stomach, or normal amount of these substances in a compromised stomach can be causative factors in ulcer formation. The stomach defends itself from these fluids in several ways. One way is by producing mucus, a lubricant-like coating which shields stomach tissues. Another way is by producing bicarbonate which neutralizes and breaks down digestive fluids into substances less harmful to stomach tissue. Finally, blood circulation to the stomach lining, cell renewal, and cell repair also help protect the stomach.

*H. pylori* is a spiral-shaped bacterium found in the stomach. It has been shown that this bacterium (along with acid secretions) can damage stomach and duodenal tissue, causing inflammation and ulcers.

*H. pylori* survives in the stomach because it produces the enzyme urease. Urease generates substances that neutralize the stomach's acid, thereby enabling the bacterium to survive. Because of its shape and the way it moves, *H. pylori* can penetrate the stomach's protective mucous lining. Here, it can produce substances that weaken the stomach's protective mucus and make the stomach cells more susceptible to the damaging effects of acid and pepsin.

The bacterium can also attach to stomach cells further weakening the stomach's defensive mechanisms and producing local inflammation. For reasons not completely understood, *H. pylori* can also stimulate the stomach to produce more acid.

Excess stomach acid and other irritating factors can cause inflammation of the upper end of the duodenum, the duodenal bulb. In some people, over long periods of time, this inflammation results in production of stomach-like cells called duodenal gastric metaplasia. *H. pylori* then attacks these cells causing further tissue damage and inflammation, which may result in an ulcer.

Within weeks of infection with *H. pylori*, most people develop gastritis, an inflammation of the stomach lining. However, most people will never have symptoms or problems related to the infection. It is not known what is different in those people who develop *H. pylori*-related symptoms or ulcers. Hereditary or environmental factors may cause some individuals to develop problems. Alternatively, symptoms and ulcers may result from infection with more virulent strains of bacteria.

The most common ulcer symptom is a gnawing or burning pain in the abdomen between the breastbone and the navel. The pain often occurs between meals and in the early hours of the morning. It may last from a few minutes to a few hours and may be relieved by eating or by taking antacids.

Less common ulcer symptoms include nausea, vomiting, and loss of appetite and weight. Bleeding from ulcers may occur in the stomach and duodenum. Sometimes patients are unaware that they have a bleeding ulcer, because blood loss is slow and blood may not be obvious in the stool. Such patients can feel tired and weak. If the bleeding is heavy, blood will appear in vomit or stool. Stool containing blood appears tarry or black.

Ulcers can be diagnosed by performing endoscopic and x-ray examinations, and well as by for testing for *H. pylori*. An upper GI series can be used to diagnose ulcers. An upper GI series involves taking an x-ray of the esophagus, stomach, and duodenum to locate an ulcer. To make the ulcer visible on the x-ray image, the patient swallows a chalky liquid called barium.

An alternative diagnostic test is endoscopy during which the patient is lightly sedated and the doctor inserts a small flexible instrument with a camera on the end through the mouth into the esophagus, stomach, and duodenum. With this procedure, the entire upper GI tract can be viewed. Ulcers or other conditions can be diagnosed and photographed, and tissue can be taken for biopsy, if necessary.

Stomach and duodenal ulcers can be treated with H2-blockers, acid (proton) pump inhibitors, and mucosal protective agents. When treating *H. pylori*, these medications are used in combination with antibiotics.

H2-blockers reduce the amount of acid the stomach produces by blocking histamine, a powerful stimulant of acid secretion. Unfortunately, H2-blockers require several weeks to significantly reduce ulcer pain. Furthermore, treatment with H2-blockers lasts 6 to 8 weeks. Nizatidine (AXID®) is approved for treatment of duodenal ulcers but is not yet approved for treatment of stomach ulcers. H2-blockers that are approved to treat both stomach and duodenal ulcers are include Cimetidine (TAGAMET®), Ranitidine (ZANTAC®) and Famotidine (PEPCID®).

Like H2-blockers, acid (proton) pump inhibitors modify the stomach's production of acid. However, acid pump inhibitors more completely block stomach acid production by stopping the stomach's acid pump, the final step of acid secretion. The FDA has approved use of omeprazole for short-term treatment of ulcer disease.

Mucosal protective medications protect the stomach's mucous lining from acid. Unlike H2-blockers and acid pump inhibitors, protective agents do not inhibit the release of acid. These medications shield the stomach's mucous lining from the damage of acid. Two commonly prescribed protective agents are:

Sucralfate (CARAFATE®). This medication adheres to the ulcer, providing a protective barrier that allows the ulcer to heal and inhibits further damage by stomach acid. Sucralfate is approved for short-term treatment of duodenal ulcers and for maintenance treatment.

Misoprostol (CYTOTEC®). This synthetic prostaglandin, a substance naturally produced by the body, protects the stomach lining by increasing mucus and bicarbonate production and by enhancing blood flow to the stomach. It is approved only for the prevention of NSAID-induced ulcers.

Two common non-prescription protective medications are: Antacids. Antacids can offer temporary relief from ulcer pain by neutralizing stomach acid. They may also have a mucosal protective role. Many brands of antacids are available without prescription. Bismuth Subsalicylate. Bismuth subsalicylate has both a protective effect and an antibacterial effect against *H. pylori*.

The discovery of the link between ulcers and *H. pylori* has resulted in a new treatment option. Now, in addition to treatment aimed at decreasing the production of stomach acid, doctors may prescribe antibiotics for patients with *H. pylori*. This treatment is a dramatic medical advance because eliminating *H. pylori* means the ulcer may now heal and most likely will not come back.

Various treatment regimes can be used, lasting from two to eight weeks. Thus use of a two week, triple therapy is known. This regimen can eradicate much of the *H. pylori* bacteria and can reduce the risk of recurrence of a duodenal ulcers. Patients with stomach ulcers that are not associated with NSAIDs can also benefit from bacterial eradication. While triple therapy is effective, it is sometimes difficult to follow because the patient must take three different medications four times each day for 2 weeks.

In addition, the treatment commonly causes side effects such as yeast infection in women, stomach upset, nausea, vomiting, bad taste, loose or dark bowel movements, and dizziness. The 2-week, triple therapy combines two antibiotics, tetracycline (e.g., ACHROMYCIN® or SUMYCIN®) and metronidazole (e.g., FLAGYL®) with bismuth subsalicylate (PEPTO-BISMOL®). Some doctors may add an acid-suppressing drug to relieve ulcer pain and promote ulcer healing. In some cases, doctors may substitute amoxicillin (e.g., AMOXIL® or TRIMOX®) for tetracycline or if they expect bacterial resistance to metronidazole, other antibiotics such as clarithromycin (BIAXIN®).

As an alternative to triple therapy, two-week, dual therapies are also known. Dual therapy is simpler for patients to follow and causes fewer side effects. A dual therapy might include an antibiotic, such as amoxicillin or clarithromycin, with omeprazole, a drug that stops the production of acid. Unfortunately, it can require from four to eight weeks (i.e. using bismuth, metronidazole, tetracycline) or even longer (i.e. using H2 or proton pump inhibitor) to effectively treat a peptic ulcer with current therapies.

In most cases, anti-ulcer medicines heal ulcers quickly and effectively. Eradication of *H. pylori* prevents most ulcers from recurring. However, patients who do not respond to medication or who develop complications may require surgery. While surgery is usually successful in healing ulcers and preventing their recurrence and future complications, problems can sometimes result.

At present, standard open surgery is performed to treat ulcers. In the future, surgeons may use laparoscopic methods. A laparoscope is a long tube-like instrument with a camera that allows the surgeon to operate through small incisions while watching a video monitor. The common types of surgery for ulcers are vagotomy, pyloroplasty, and antrectomy.

A vagotomy involves cutting the vagus nerve, a nerve that transmits messages from the brain to the stomach. Interrupting the messages sent through the vagus nerve reduces acid secretion. However, the surgery may also interfere with stomach emptying. The newest variation of the surgery involves cutting only parts of the nerve that control the acid-secreting cells of the stomach, thereby avoiding the parts that influence stomach emptying.

In an antrectomy the lower part of the stomach (antrum), which produces a hormone that stimulates the stomach to secrete digestive juices is removed. Sometimes a surgeon may also remove an adjacent part of the stomach that secretes pepsin and acid. A vagotomy is usually done in conjunction with an antrectomy.

Pyloroplasty is another surgical procedure that may be performed along with a vagotomy. Pyloroplasty enlarges the opening into the duodenum and small intestine (pylorus), enabling contents to pass more freely from the stomach.

The complications of ulcers can include bleeding, perforation of the organ walls, and narrowing and obstruction of digestive tract passages. As an ulcer eats into the muscles of the stomach or duodenal wall, blood vessels may also be damaged, which causes bleeding. If the affected blood vessels are small, the blood may slowly seep into the digestive tract. Over a long period of time, a person may become anemic and feel weak, dizzy, or tired. If a damaged blood vessel is large, bleeding is dangerous and requires prompt medical attention. Symptoms include feeling weak and dizzy when standing, vomiting blood, or fainting. The stool may become a tarry black color from the blood. Most bleeding ulcers can be treated endoscopically. The ulcer is located and the blood vessel is cauterized with a heating device or injected with material to stop bleeding. If endoscopic treatment is unsuccessful, surgery may be required.

Sometimes an ulcer eats a hole in the wall of the stomach or duodenum. Bacteria and partially digested food can spill through the opening into the sterile abdominal cavity (peritoneum). This causes peritonitis, an inflammation of the abdominal cavity and wall. A perforated ulcer that can cause sudden, sharp, severe pain usually requires immediate hospitalization and surgery.

Ulcers located at the end of the stomach where the duodenum is attached, can cause swelling and scarring, which can narrow or close the intestinal opening. This obstruction can prevent food from leaving the stomach and entering the small intestine. As a result, a person may vomit the contents of the stomach. Endoscopic balloon dilation, a procedure that uses a balloon to force open a narrow passage, may be performed. If the dilation does not relieve the problem, then surgery may be necessary.

Thus, there are numerous deficiencies and drawbacks associated with the current therapies for both peptic ulcers and for gastro esophageal reflux disease.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a $LD_{50}$ in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1996) (where the stated $LD_{50}$ of *botulinum* toxin type A of 0.3 ng equals 1 U is corrected for the fact that about 0.05 ng of BOTOX® equals 1 unit). One unit (U) of *botulinum* toxin is defined as the $LD_{50}$ upon intraperitoneal injection into female Swiss Webster mice weighing 18 to 20 grams each.

Available from Allergan, Inc., of Irvine, Calif. under the tradename BOTOX® in 100 unit vials Seven immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. Moyer E et al., *Botulinum Toxin Type B: Experimental and Clinical Experience*, being chapter 6, pages 71-85 of "Therapy With *Botulinum* Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of *botulinum* toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype $C_1$ was originally thought to cleave syntaxin, but was found to cleave syntaxin and SNAP-25. Each of the *botulinum* toxins specifically cleaves a different bond, except *botulinum* toxin type B (and tetanus toxin) which cleave the same bond.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type $C_1$ has been shown to cleave both syntaxin and SNAP-25. These differences in mechanism of action may affect the relative potency and/or duration of action of the various *botulinum* toxin serotypes. Apparently, a substrate for a *botulinum* toxin can be found in a variety of different cell types. See e.g. Gonelle-Gispert, C., et al., *SNAP-25a and-25b isoforms are both expressed in insulin-secreting cells and can function in insulin secretion*, Biochem J. 1; 339 (pt 1):159-65: 1999, and Boyd R. S. et al., *The effect of botulinum neurotoxin-B on insulin release from a ∃-cell line*, and Boyd R. S. et al., *The insulin secreting ∃-cell line, HIT-15, contains SNAP-25 which is a target for botulinum neurotoxin-A*, both published at *Mov Disord*, 10(3):376: 1995 (pancreatic islet B cells contains at least SNAP-25 and synaptobrevin).

The molecular weight of the *botulinum* toxin protein molecule, for all seven of the known *botulinum* toxin serotypes, is about 150 kD. Interestingly, the *botulinum* toxins are released by *Clostridial* bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. *Botulinum* toxin types B and $C_1$ is apparently produced as only a 700 kD or 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

All the *botulinum* toxin serotypes are made by *Clostridium botulinum* bacteria as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for a lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy.

*Botulinum* toxins and toxin complexes can be obtained from, for example, List Biological Laboratories, Inc., Campbell, Calif.; the Centre for Applied Microbiology and Research, Porton Down, U.K.; WAKO® (Osaka, Japan), as well as from SIGMA-ALDRICH® of St Louis, Mo. Commercially available *botulinum* toxin containing pharmaceutical compositions include BOTOX® (*Botulinum* toxin type A neurotoxin complex with human serum albumin and sodium chloride) available from ALLERGAN® Inc., of Irvine, Calif. in 100 unit vials as a lyophilized powder to be reconstituted with 0.9% sodium chloride before use), DYSPORT® (*Clostridium botulinum* type A toxin haemagglutinin complex with human serum albumin and lactose in the formulation), available from IPSEN® Limited, Berkshire, U.K. as a powder to be reconstituted with 0.9% sodium chloride before use), and MYOBLOC® (an injectable solution comprising *botulinum* toxin type B, human serum albumin, sodium succinate, and sodium chloride at about pH 5.6, available from ELAN® Corporation, Dublin, Ireland).

The success of *botulinum* toxin type A to treat a variety of clinical conditions has led to interest in other *botulinum* toxin serotypes. Additionally, pure *botulinum* toxin has been used to treat humans. see e.g. Kohl A., et al., *Comparison of the effect of botulinum toxin A (Botox (R)) with the highly-purified neurotoxin (NT 201) in the extensor digitorum brevis muscle test*, Mov Disord 2000; 15(Suppl 3):165. Hence, a pharmaceutical composition can be prepared using a pure *botulinum* toxin.

The type A *botulinum* toxin is known to be soluble in dilute aqueous solutions at pH 4-6.8. At pH above about 7 the stabilizing nontoxic proteins dissociate from the neurotoxin, resulting in a gradual loss of toxicity, particularly as the pH and temperature rise. Schantz E. J., et al *Preparation and characterization of botulinum toxin type A for human treatment* (in particular pages 44-45), being chapter 3 of Jankovic, J., et al, *Therapy with Botulinum Toxin*, Marcel Dekker, Inc (1994).

The *botulinum* toxin molecule (about 150 kDa), as well as the *botulinum* toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527: 1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681: 1987. Thus, when adequate concentrations are used, stimulus-evoked release of most neurotransmitters is blocked by *botulinum* toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324: 1985; Habermann E., *Inhibition by Tetanus and Botulinum A Toxin of the release of [$^3$H]Noradrenaline and [$^3$H]GABA From Rat Brain Homogenate*, Experientia 44; 224-226: 1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251: 1981, and; Jankovic J. et al., *Therapy With Botulinum Toxin*, Marcel Dekker, Inc., (1994), page 5.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by non-proteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\leq 3 \times 10^7$ U/mg, an $A_{260}/A_{278}$ of less than 0.60 and a distinct pattern of banding on gel electrophoresis. The known Schantz process can be used to obtain crystalline *botulinum* toxin type A, as set forth in Schantz, E. J., et al, *Properties and use of Botulinum toxin and Other Microbial Neurotoxins in Medicine*, Microbiol Rev. 56; 80-99: 1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of 1-2×10$^8$ LD$_{50}$ U/mg or greater; purified *botulinum* toxin type B with an approximately 156 kD molecular weight with a specific potency of 1-2×10$^8$ LD$_{50}$ U/mg or greater, and; purified *botulinum* toxin type F with an approximately 155 kD molecular weight with a specific potency of 1-2×10$^7$ LD$_{50}$ U/mg or greater.

Either the pure *botulinum* toxin (i.e. the 150 kilodalton *botulinum* toxin molecule) or the toxin complex can be used to prepare a pharmaceutical composition. Both molecule and complex are susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from ALLERGAN® Inc., of Irvine, Calif.). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53: 1997.

*Botulinum* toxins have been used in clinical settings for the treatment of neuromuscular disorders characterized by hyperactive skeletal muscles. *Botulinum* toxin type A (BOTOX®) was approved by the U.S. Food and Drug Administration in 1989 for the treatment of essential blepharospasm, strabismus and hemifacial spasm in patients over the age of twelve. In 2000 the FDA approved commercial preparations of type A (BOTOX®) and type B *botulinum* toxin (MYOBLOC®) serotypes for the treatment of cervical dystonia, and in 2002 the FDA approved a type A *botulinum* toxin (BOTOX®) for the cosmetic treatment of certain hyperkinetic (glabellar) facial wrinkles. Clinical effects of peripheral intramuscular *botulinum* toxin type A are usually seen within one week of injection and sometimes within a few hours. The typical duration of symptomatic relief (i.e. flaccid muscle paralysis) from a single intramuscular injection of *botulinum* toxin type A can be about three months, although in some cases the effects of a *botulinum* toxin induced denervation of a gland, such as a salivary gland, have been reported to last for several years. For example, it is known that *botulinum* toxin type A can have an efficacy for up to 12 months (Naumann M., et al., *Botulinum toxin type A in the treatment of focal, axillary and palmar hyperhidrosis and other hyperhidrotic conditions*, European J. Neurology 6 (Supp 4): S111-S115: 1999), and in some circumstances for as long as 27 months. Ragona, R. M., et al., *Management of parotid sialocele with botulinum toxin*, The Laryngoscope 109: 1344-1346: 1999. However, the usual duration of an intramuscular injection of BOTOX® is typically about 3 to 4 months.

It has been reported that a *botulinum* toxin type A has been used in diverse clinical settings, including for example as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patient's with Parkinson's disease, although it has been reported that results have not been impressive. Marjama-Lyons, J., et al., *Tremor-Predominant Parkinson's Disease*, Drugs & Aging 16(4); 273-278: 2000.

Treatment of certain gastrointestinal and smooth muscle disorders with a *botulinum* toxin are known. See e.g. U.S. Pat. Nos. 5,427,291 and 5,674,205 (Pasricha). Additionally, transurethral injection of a *botulinum* toxin into a bladder sphincter to treat a urination disorder is known (see e.g. Dykstra, D. D., et al, *Treatment of detrusor-sphincter dyssynergia with botulinum A toxin: A double-blind study*, Arch Phys Med Rehabil 1990 January; 71:24-6), as is injection of a *botulinum* toxin into the prostate to treat prostatic hyperplasia. See e.g. U.S. Pat. No. 6,365,164 (Schmidt). See also U.S. Pat. No. 7,238,357 (Barron), entitled "Methods for treating ulcers and gastroesophageal reflux disease".

U.S. Pat. No. 5,766,605 (Sanders) proposes the treatment of various autonomic disorders, such as hypersalivation and rhinitis, with a *botulinum* toxin. Additionally, It is known that nasal hypersecretion is predominantly caused by over activity of nasal glands, which are mainly under cholinergic control and it has been demonstrated that application of *botulinum* toxin type A to mammalian nasal mucosal tissue of the maxillary sinus turbinates can induce a temporary apoptosis in the nasal glands. Rohrbach S., et al., *Botulinum toxin type A induces apoptosis in nasal glands of guinea pigs*, Ann Otol Rhinol Laryngol 2001 November; 110(11):1045-50. Furthermore, local application of *botulinum* toxin A to a human female patient with intrinsic rhinitis resulted in a clear decrease of the nasal hypersecretion within five days. Rohrbach S., et al., *Minimally invasive application of botulinum toxin type A in nasal hypersecretion*, J Oto-Rhino-Laryngol 2001 November-December; 63(6):382-4.

Various afflictions, such as hyperhydrosis and headache, treatable with a *botulinum* toxin are discussed in WO 95/17904 (PCT/US94/14717) (Aoki). EP 0 605 501 B1 (Graham) discusses treatment of cerebral palsy with a *botulinum* toxin and U.S. Pat. No. 6,063,768 (First) discusses treatment of neurogenic inflammation with a *botulinum* toxin.

In addition to having pharmacologic actions at the peripheral location, *botulinum* toxins can also have inhibitory effects in the central nervous system. Work by Weigand et al, ($^{125}$*I-labelled botulinum A neurotoxin:pharmacokinetics in cats after intramuscular injection*, Nauny-Schmiedeberg's Arch. Pharmacol. 1976; 292, 161-165), and Habermann, ($^{125}$*I-labelled Neurotoxin from clostridium botulinum A: preparation, binding to synaptosomes and ascent to the spinal cord*, Nauny-Schmiedeberg's Arch. Pharmacol. 1974; 281, 47-56) showed that *botulinum* toxin is able to ascend to the spinal area by retrograde transport. As such, a *botulinum* toxin injected at a peripheral location, for example intramuscularly, may be retrograde transported to the spinal cord.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

U.S. Pat. No. 5,989,545 discloses that a modified clostridial neurotoxin or fragment thereof, preferably a *botu*-

*linum* toxin, chemically conjugated or recombinantly fused to a particular targeting moiety can be used to treat pain by administration of the agent to the spinal cord.

A *botulinum* toxin has also been proposed for the treatment of hyperhydrosis (excessive sweating, U.S. Pat. No. 5,766, 605), headache (U.S. Pat. No. 6,458,365), sinus headache (U.S. Pat. No. 6,838,434), migraine headache (U.S. Pat. No. 5,714,468), post-operative pain and visceral pain (U.S. Pat. No. 6,464,986), pain by intraspinal administration (U.S. Pat. No. 6,113,915), Parkinson's disease by intracranial administration (U.S. Pat. No. 6,306,403), hair growth and hair retention (U.S. Pat. No. 6,299,893), obesity (U.S. Pat. No. 7,737, 109), psoriasis and dermatitis (U.S. Pat. No. 5,670,484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437, 291, including injection of a *botulinum* toxin into the upper and lower esophageal, pyloric and anal sphincters)), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977), various neurological and neuropsychiatric disorders (published U.S. patent application 2005 0147626 A1) and for premenstrual disorders (published U.S. patent application 2006 0083758 A1). Additionally, controlled release toxin implants are known (U.S. Pat. Nos. 6,306,423 and 6,312,708).

It has been reported that that intravenous injection of a *botulinum* toxin causes a decline of pentagastrin stimulated acid and pepsin secretion in rats. Kondo T., et al., *Modification of the action of pentagastrin on acid secretion by botulinum toxin*, Experientia 1977; 33:750-1. Additionally it has been speculated that a *botulinum* toxin can be used to reduce a gastrointestinal secretion, such as a gastric secretion. See pages 16-17 of WO 95/17904. Furthermore, a *botulinum* toxin has been proposed for the treatment of disorders of gastrointestinal muscle in the enteric nervous system disorder (U.S. Pat. No. 5,437,291) and well as to treat various autonomic disorders (U.S. Pat. No. 5,766,605). *Botulinum* toxin has been injected into the fundus of the stomach of dogs. Wang Z., et al., *Effects of botulinum toxin on gastric myoelectrical and vagal activities in dogs*, Gastroenterology 2001 April; 120(5 Suppl 1):A-718. Additionally, intramuscular injection of a *botulinum* toxin into the gastric antrum has been proposed as a treatment for obesity. See e.g. Gui D., et al., *Effects of botulinum toxin on gastric emptying and digestive secretions. A possible tool for correction of obesity?*, Naunyn Schmiedebergs Arch Pharmacol 2002 June; 365(Suppl 2):R22; Albanese A., et al., *The use of botulinum toxin on smooth muscles*, Eur J Neurol 1995 November; 2(Supp 3):29-33, and; Gui D., et al., *Botulinum toxin injected in the gastric wall reduces body weight and food intake in rats*, Aliment Pharmacol Ther 2000 June; 14(6):829-834. Furthermore, *botulinum* toxin type A has been proposed as a therapeutic application for the control of secretion in the stomach. Rossi S., et al., *Immunohistochemical localization of SNAP-25 protein in the stomach of rat*. Naunyn Schmiedebergs Arch Pharmacol 2002; 365(Suppl 2):R37.

Significantly, it has been reported that injection of a *botulinum* toxin into the lower esophageal sphincter for the treatment of achalasia results in the formation of ulcers in the esophagus. Eaker, E.Y., et al., *Untoward effects of esophageal botulinum toxin injection in the treatment of achalasia*, Dig Dis Sci 1997 April; 42(4):724-7. It is know to inject a *botulinum* toxin into a spastic pyloric sphincter of a patient with a prepyloric ulcer in order to permit the pyloric muscle to open.

Wiesel P. H. et al., *Botulinum toxin for refractory postoperative pyloric spasm*, Endoscopy 1997; 29(2):132.

Tetanus toxin, as wells as derivatives (i.e. with a non-native targeting moiety), fragments, hybrids and chimeras thereof can also have therapeutic utility. The tetanus toxin bears many similarities to the *botulinum* toxins. Thus, both the tetanus toxin and the *botulinum* toxins are polypeptides made by closely related species of *Clostridium* (*Clostridium tetani* and *Clostridium botulinum*, respectively). Additionally, both the tetanus toxin and the *botulinum* toxins are dichain proteins composed of a light chain (molecular weight about 50 kD) covalently bound by a single disulfide bond to a heavy chain (molecular weight about 100 kD). Hence, the molecular weight of tetanus toxin and of each of the seven *botulinum* toxins (non-complexed) is about 150 kD. Furthermore, for both the tetanus toxin and the *botulinum* toxins, the light chain bears the domain which exhibits intracellular biological (protease) activity, while the heavy chain comprises the receptor binding (immunogenic) and cell membrane translocational domains.

Further, both the tetanus toxin and the *botulinum* toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of *botulinum* toxin by peripheral cholinergic neurons results in little if any retrograde transport, inhibition of acetylcholine exocytosis from the intoxicated peripheral motor neurons and a flaccid paralysis.

Finally, the tetanus toxin and the *botulinum* toxins resemble each other in both biosynthesis and molecular architecture. Thus, there is an overall 34% identity between the protein sequences of tetanus toxin and *botulinum* toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158: 1990.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore are economical and effective methods for treating gastric disorders, including delayed gastric emptying, GERD and peptic ulcers with a *botulinum* toxin, such as a *botulinum* neurotoxin.

SUMMARY

The present invention meets this need and provides methods for treating gastric disorders, such as gastroesophageal reflux disease (GERD) by intramuscular, subcutaneous or intradermal administration of a *botulinum* toxin to a patient with a gastric disorder.

According to the present invention, the *botulinum* toxin is one of the *botulinum* toxin types A, B, $C_1$, D, E, F and G and is preferably *botulinum* toxin type A. The *botulinum* toxin (as a complex or as a pure, about 150 kDa protein) can be formulated with the excipient (such as an albumin) in an amount of between about 1 unit and about 13,000 units of the *botulinum* toxin. Preferably, the quantity of the *botulinum* toxin administered is between about 5 units and about 500 units of a *botulinum* toxin type A. Where the *botulinum* toxin is *botulinum* toxin type B, preferably, the quantity of the *botulinum* toxin associated with the carrier can be between about 250 units and about 13,000 units of a *botulinum* toxin type B.

The amount of a *botulinum* toxin administered within the scope of the present invention during a given period can be between about $10^{-3}$ U/kg and about 35 U/kg for a *botulinum* toxin type A and up to about 2000 U/kg for other *botulinum* toxins, such as a *botulinum* toxin type B. 35 U/kg or 2000 U/kg is an upper limit because it approaches a lethal dose of certain neurotoxins, such as *botulinum* toxin type A or *botulinum* toxin type B, respectively. Thus, it has been reported that about 2000 units/kg of a commercially available *botulinum* toxin type B preparation approaches a primate lethal dose of type B *botulinum* toxin. Meyer K. E. et al, *A Comparative Systemic Toxicity Study of Neurobloc in Adult Juvenile Cynomolgus Monkeys*, Mov. Disord 15(Suppl 2); 54; 2000.

Preferably, the amount of a type A *botulinum* toxin administered is between about $10^{-2}$ U/kg and about 25 U/kg. Preferably, the amount of a type B *botulinum* toxin administered during a given period is between about $10^{-2}$ U/kg and about 1000 U/kg, since it has been reported that less than about 1000 U/kg of type B *botulinum* toxin can be intramuscularly administered to a primate without systemic effect. Ibid. More preferably, the type A *botulinum* toxin is administered in an amount of between about $10^{-1}$ U/kg and about 15 U/kg. Most preferably, the type A *botulinum* toxin is administered in an amount of between about 1 U/kg and about 10 U/kg. In many instances, an administration of from about 1 units to about 500 units of a *botulinum* toxin type A, provides effective and long lasting therapeutic relief. More preferably, from about 5 units to about 300 units of a *botulinum* toxin, such as a *botulinum* toxin type A, can be used and most preferably, from about 10 units to about 200 units of a neurotoxin, such as a *botulinum* toxin type A, can be locally administered into a target tissue with efficacious results. In a particularly preferred embodiment of the present invention from about 20 units to about 100 units of a *botulinum* toxin, such as *botulinum* toxin type A, can be administered with therapeutically effective results.

The *botulinum* toxin can be made by *Clostridium botulinum*. Additionally, the *botulinum* toxin can be a modified *botulinum* toxin, that is a *botulinum* toxin that has at least one of its amino acids deleted, modified or replaced, as compared to the native or wild type *botulinum* toxin. Furthermore, the *botulinum* toxin can be a recombinant produced *botulinum* toxin or a derivative or fragment thereof.

A method according to our invention can be carried out by administration of a *botulinum* toxin to a patient with a gastric disorder. Notably, the *botulinum* toxin is administered to a head, neck or shoulder location of a patient to provide a therapeutic effect upon a gastric (i.e. GI or digestive system) disorder. Thus, the *botulinum* toxin is not administered so as to provide a therapeutic effect at the local site of administration of the *botulinum* toxin. Quiet to the contrary: it is my discovery that administration of a *botulinum* toxin (as by intramuscular administration) to a head, neck or shoulder location (i.e. to an intramuscular site to one or more of the muscles shown in FIG. 1, and/or subcutaneously or intradermally at or in the vicinity of the FIG. 1 muscles) has a therapeutic effect upon a distant gastric tissue site, as determined by alleviation of a gastric disorder, such as GERD or delayed gastric emptying. The *botulinum* toxin (as either a complex or as a pure [i.e. about 150 kDa molecule] can be a *botulinum* toxin A, B, C, D, E, F or G. Administration of the *botulinum* toxin can be by a transdermal route (i.e. by application of a *botulinum* toxin in a cream, patch or lotion vehicle), subdermal route (i.e. subcutaneous or intramuscular), or intradermal route of administration.

A hypothesized physiological reason for the efficacy of my invention is that the head, neck and/or administration of a *botulinum* toxin according to my invention reduces, inhibits and/or eliminates sensory input (afferent) from the periphery into the central nervous system (including to the brain) which input kindles, generates, exacerbates and/or facilitates development or maintenance of a gastric disorder in a patient.

The dose of a *botulinum* used according to the present invention is less than the amount of a *botulinum* toxin that would be used to paralyze a muscle, since an intent of a method according to the present invention is not to paralyze a muscle but to reduce a sensory output from sensory neurons located in or on a muscle, or in or under the skin.

The present invention encompasses a method for treating a gastric disorder by administering a *botulinum* toxin to a head, neck and/or shoulder location of a patient with a gastric disorder, thereby treating the gastric disorder. The *botulinum* toxin can be a *botulinum* toxins types A, B, C, D, E, F or G. Preferably, the *botulinum* toxin is a *botulinum* toxin type A. The *botulinum* toxin administered can be a *botulinum* toxin complex (i.e. from about 300 kDa to about 900 kDa in molecular weight) or a pure *botulinum* toxin, that is the about 150 kDa neurotoxic component of a *botulinum* toxin complex.

The gastric disorder treated can be a digestive disorder. The gastric disorder treated can be, for example, Crohn's disease, diverticulosis, diverticulitis, gallstones, GERD hiatal hernia, heartburn, gastric stasis, gastric emptying, pyloric valve malfunction or spasm, a GI sphincter malfunction or spasm, *H. pylori* ulcer, peptic ulcer, irritable bowel syndrome, stomach ulcer, duodenal ulcer, colitis and/or ulcerative colitis.

Administration of a *botulinum* toxin according to the method disclosed herein can be by intramuscular administration of the *botulinum* toxin to a head, neck and/or shoulder muscle of the patient. In some cases the patient can have both a gastric disorder and a headache, such as a tension headache, migraine, cluster headache, sinus headache and cervogenic headache.

A detailed method according to the present invention can be a method for treating GERD or delayed gastric emptying by intramuscular administration a therapeutically effective amount of a *botulinum* toxin to a head, neck and/or shoulder muscle of a patient with GERD or delayed gastric emptying, thereby treating the GERD or delayed gastric emptying. The intramuscular administration can be to a frontalis, glabellar, occipitalis, temporalis, masseter, trapezius, semispinalis and/or splenius capitis muscles. The *botulinum* toxin can be administered in an amount between about 5 units and about 13,000 units, depending upon factors such as the *botulinum* toxin serotype used, the mass of the patient treated and the severity of the patient's condition.

A further detailed embodiment of a method for treating GERD or delayed gastric emptying according to the present invention can be carried by intramuscular administration a therapeutically effective amount of a *botulinum* toxin type A to each of the frontalis, glabellar, occipitalis, temporalis, masseter, trapezius, semispinalis and splenius capitis muscles of a patient with GERD or delayed gastric emptying, thereby treating the GERD or the delayed gastric emptying.

DEFINITIONS

The following definitions apply herein.

"About" means plus or minus ten percent of the value so qualified.

"Biocompatible" means that there is an insignificant inflammatory or immunogenic response from use of a *botulinum* toxin according to the present invention.

"Biologically active compound" means a compound which can effect a beneficial change in the subject to which it is administered. For example, "biologically active compounds" include neurotoxins.

"Effective amount" as applied to the biologically active compound (such as a *botulinum* toxin) means that amount of the compound which is generally sufficient to effect a desired change in a patient. For example, where the desired effect is treatment of a gastric disorder, an effective amount of the compound is that amount which causes at least a substantial alleviation of the gastric disorder, as observed clinically, without a significant systemic toxicity resulting.

"Gastric Disorder" means a digestive disease, disorder or condition, including Crohn's disease, diverticulosis, diverticulitis, gallstones, gastroesophageal reflux disease (GERD), hiatal hernia, heartburn, gastric stasis, delayed gastric emptying, pyloric valve (or other GI sphincter) malfunction or spasm, *H. pylori* and peptic ulcers, irritable bowel syndrome, stomach and duodenal ulcers, colitis, including ulcerative colitis.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron. Examples of neurotoxins include *botulinum* toxins, tetanus toxins, saxitoxins, and tetrodotoxin.

"Treatment" means any treatment of a disease in a mammal, and includes: (i) preventing the disease from occurring or; (ii) inhibiting the disease, i.e., arresting its development; (iii) relieving the disease, i.e., reducing the incidence of symptoms of or causing regression of the disease.

BRIEF DESCRIPTION OF THE FIGURE

The following drawing illustrates aspects of the invention.

FIG. 1 is a diagrammatic representation of the human musculature of the head, neck and shoulders showing the locations where a *botulinum* toxin can be administered (as by intramuscular injection) in a practise of a method according to the invention disclosed herein.

DESCRIPTION

The present invention is based upon the discovery of a gastric disorder can be successfully treated by administration of a *botulinum* toxin to a head, neck or shoulder location of a patient. Thus, I have found that gastroesophageal reflux disease and/or symptoms thereof can be treated by administration, such as by intramuscular injection, of a *botulinum* toxin to a head, neck or shoulder location of a patient. Thus, I have discovered that administration of a *botulinum* toxin, such as a *botulinum* toxin type A, permits delivery of therapeutic amounts of a bioactive *botulinum* toxin to treat a gastric disorder. Typically, within a few hours or days after administration of a *botulinum* toxin the gastric disorder, such as GERD, enters remission and/or it's symptoms are alleviated.

My discovery that administration of a *botulinum* toxin can be used to treat a gastric disorder such as GERD is surprising because of the considerable anatomical distance and apparent lack of systemic connection or control/biofeedback mechanisms between the head, neck and/or shoulder location to which the *botulinum* toxin is administered and the target GI tissue to be treated.

The therapeutic dose of administered *botulinum* toxin is such that there are nominal or insignificant systemic effects due to any *botulinum* toxin which passes into the circulatory system.

Preferably, a the *botulinum* toxin used to practice a method within the scope of the present invention is a *botulinum* neurotoxin, such as one of the serotype A, B, C, D, E, F or G *botulinum* toxins. Preferably, the *botulinum* toxin used is *botulinum* toxin type A, because of its high potency in humans, ready availability, and known safe and efficacious use for treatment of various disorders.

The present invention includes within its scope the use of any *botulinum* neurotoxin which has a therapeutic effect to treat a gastric disorder according to the present invention. For example, neurotoxins made by any of the species of the toxin producing *Clostridium* bacteria, such as *Clostridium botulinum, Clostridium butyricum*, and *Clostridium beratti* can be used or adapted for use in the methods of the present invention. Additionally, all of the *botulinum* serotypes A, B, C, D, E, F and G can be advantageously used in the practice of the present invention, although type A is the most preferred serotype, as explained above.

The present invention includes within its scope: (a) a *botulinum* neurotoxin complex as well as a pure *botulinum* neurotoxin obtained or processed by bacterial culturing, toxin extraction, concentration, preservation, freeze drying and/or reconstitution and; (b) modified or recombinant *botulinum* neurotoxin, that is *botulinum* neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of *botulinum* neurotoxins so made, and includes *botulinum* neurotoxins with one or more attached targeting moieties for a cell surface receptor present on a cell.

*Botulinum* toxins for use according to the present invention can be stored in lyophilized or vacuum dried form in containers under vacuum pressure. Prior to lyophilization the *botulinum* toxin can be combined with pharmaceutically acceptable excipients, stabilizers and/or carriers, such as albumin. The lyophilized or vacuum dried material can be reconstituted with saline or water.

Methods for determining the appropriate dosage is generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

EXAMPLES

The following examples set forth specific compositions and methods encompassed by the present invention and are not intended to limit the scope of the present invention.

Example 1

Method for Treating a Peptic Ulcer

A 52 year old male presents with a burning pain in the abdomen between the breastbone and the navel and he relates that the pain often occurs between meals and in the early hours of the morning. The patient also complains of nausea and loss of appetite. Endoscopy, supplemented by barium x-ray, confirms the presence of a gastric ulcer. The ulcer proves intractable to H2-blockers as well as to antibiotics to *H. pylori*. The patient is treated by intramuscular administration of a 110 units of BOTOX® (*botulinum* toxin type A) to head, neck and/or shoulder muscles. Within two weeks the symptoms of a peptic ulcer are substantially alleviated.

Example 2

Method for Treating Gastroesophageal Reflux Disease

A 42 year male presents with heartburn and regurgitation and is diagnosed with GERD. The patient is treated by administration of a *botulinum* toxin using the same injection protocol used for the treatment of a migraine headache. Thus, over 23 to 58 injection sites within 6 to 7 muscle areas from 105 units ("U") to 260 units of BOTOX® is administered, as shown by Table 1.

TABLE 1

| Muscle Area | Number of Units | Bilateral Injection | Total Dose (U) |
|---|---|---|---|
| Frontal/Glabellar | 25–40 | No | 25–40 |
| Occipitalis | 10 | Yes | 20 |
| Temporalis | 10–25 | Yes | 20–50 |
| Masseter (optional) | 0–25 | Yes | 0–50 |
| Trapezius | 10–30 | Yes | 20–60 |
| Semispinalis | 5–10 | Yes | 10–20 |
| Splenius capitis | 5–10 | Yes | 10–20 |
| Total Dose Range | | | 105–260 |

FIG. 1 shows the locations of the Table 1 muscles.

Note that, as set forth in the table above, as little as 5 units of BOTOX® can be administered, if only one muscle is injected with the *botulinum* toxin. When different serotypes or stains of a *botulinum* toxin are used different amounts may be administered. For example, about four times as much (i.e. up to about 1040 units) DYSPORT® (a *botulinum* toxin type A complex) may be administered, and up to about fifty times as much (i.e. up to about 13,000 units) MYOBLOC (a *botulinum* toxin type B complex) can be used, as the BOTOX®: DYSPORT®:MYOBLOC® units used in practise are typically 1:4:50.

Each vial of BOTOX® (ALLERGAN®, Irvine, Calif.) contains 100 U of *Clostridium botulinum* toxin type A, 0.5 mg albumin (human), and 0.9 mg sodium chloride in a sterile, vacuum-dried form without a preservative. One U corresponds to the calculated median lethal intraperitoneal dose ($LD_{50}$) in mice. The vials are stored in a freezer between −20° C. and −5° C. before use. Within a few days or by a maximum of two weeks after administration of the *botulinum* toxin the patients' symptoms of GERD have disappeared or have been substantially reduced.

Example 3

Method for Treating Delayed Gastric Emptying

A patient with delayed gastric emptying can be treated by administering a *botulinum* toxin to the patient. The administration can be by subcutaneous or intramuscular injection of from about 100 to about 300 units a *botulinum* toxin type A (i.e. Botox®) to or to the vicinity of one or more or to all of the muscles shown in FIG. 1, using the injection protocol set forth in Table 1. Within a few days or by a maximum of two weeks after the administration of the *botulinum* toxin, the patients' delayed gastric emptying disorder can disappear or be substantially reduced, and the gastric emptying can occur in a normal or near normal time frame.

Example 4

Methods for Treating Gastric Disorders

A patient can have a gastric disorder such as a digestive disease, disorder or condition, such as Crohn's disease, diverticulosis, diverticulitis, gallstones, gastroesophageal reflux disease (GERD), hiatal hernia, heartburn, gastric stasis, delayed gastric emptying, pyloric valve (or other GI sphincter) malfunction or spasm, *H. pylori* and peptic ulcers, irritable bowel syndrome, stomach and duodenal ulcers, colitis, including ulcerative colitis. The patient can be treated by administering a *botulinum* toxin. The administration can be by intramuscular injection of from about 100 to about 300 units a *botulinum* toxin type A (i.e. BOTOX®) to one or more or to all of the muscles shown in FIG. 1, using the injection protocol set forth by Table 1. Within a few days or by a maximum of two weeks after the administration of the *botulinum* toxin the patients' symptoms of the gastric disorder can disappear or be substantially reduced.

Compositions and methods according to the invention disclosed herein has many advantages, including that a *botulinum* toxin can be used to provide therapeutically effective treatment of a gastric disorder.

All references, articles, publications and patents and patent applications cited herein are incorporated by reference in their entireties.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes formulations wherein two or more neurotoxins, such as two or more *botulinum* toxins, are administered concurrently or consecutively. For example, *botulinum* toxin type A can be administered until a loss of clinical response or neutralizing antibodies develop, followed by administration of a *botulinum* toxin type B or E. Alternately, a combination of any two or more of the *botulinum* serotypes A-G can be locally administered to control the onset and duration of the desired therapeutic result. Furthermore, non-neurotoxin compounds can be administered prior to, concurrently with or subsequent to administration of the neurotoxin formulation so as to provide an adjunct effect such as enhanced or a more rapid onset of denervation before the neurotoxin, such as a *botulinum* toxin, begins to exert its therapeutic effect.

The present invention also includes within its scope the use of a neurotoxin, such as a *botulinum* toxin, in the preparation of a medicament for use to treat a gastric disorder by administration of the *botulinum* toxin to a head, neck and/or shoulder location of a patient with a gastric order.

Accordingly, the spirit and scope of the following claims should not be limited to the descriptions of the preferred embodiments set forth above.

I claim:

1. A method for treating gastroesophageal reflux disease the method comprising the step of administering a therapeutically effective amount of a *botulinum* toxin to a head, neck and/or shoulder location of a patient with gastroesophageal reflux disease by intradermal or intramuscular injection, the *botulinum* toxin reducing a symptom of the gastroesophageal reflux disease, thereby treating the gastroesophageal reflux disease, wherein the therapeutically effective amount of a *botulinum* toxin is that amount which causes at least an alleviation of a symptom of the gastroesophageal reflux disease, as observed clinically, without a systemic toxicity resulting.

2. The method of claim 1, wherein the *botulinum* toxin is selected from the group consisting of *botulinum* toxins types A, B, $C_1$, D, E, F and G.

3. The method of claim 1, wherein the *botulinum* toxin is a *botulinum* toxin type A.

4. The method of claim 1, wherein the administration step is carried out by intramuscular administration of the *botulinum* toxin to a head, neck and/or shoulder muscle of the patient.

5. The method of claim 1, wherein the patient also has a headache.

6. The method of claim 1, wherein the patient also has a headache selected from the group consisting of a tension headache, migraine, cluster headache, sinus headache and cervogenic headache.

7. The method of claim 1, wherein the *botulinum* toxin is a *botulinum* toxin complex.

8. The method of claim 1, wherein the *botulinum* toxin is a pure *botulinum* toxin.

9. A method for treating GERD, the method comprising the step of intramuscular administration of a therapeutically effective amount of a *botulinum* toxin type A to a head, neck and/or shoulder muscle of a patient with GERD, the *botulinum* toxin reducing a symptom of GERD, thereby treating GERD; wherein the therapeutically effective amount of a *botulinum* toxin is that amount which causes at least an alleviation of a symptom of GERD, as observed clinically, without a systemic toxicity resulting.

10. The method of claim 9, wherein the *botulinum* toxin administered is in an amount between about 1 unit and about 500 units.

11. The method of claim 9, wherein the *botulinum* toxin is administered to a muscle selected from the group consisting of the frontalis, glabellar, occipitalis, temporalis, masseter, trapezius, semispinalis and splenius capitis muscles.

12. A method for treating GERD, the method comprising the step of intramuscular administration therapeutically effective amount of a *botulinum* toxin type A to each of the frontalis, glabellar, occipitalis, temporalis, masseter; trapezius, semispinalis and splenius capitis muscles of a patient with GERD, the *botulinum* toxin reducing a symptom of GERD, thereby treating GERD, wherein the therapeutically effective amount of a *botulinum* toxin type A is that amount which causes at least an alleviation of a symptom of GERD, as observed clinically, without a significant systemic toxicity resulting.

* * * * *

UNITED STATES PATENT AND TRADEMARK OFFICE
CERTIFICATE OF CORRECTION

PATENT NO.       : 7,910,116 B2
APPLICATION NO.  : 11/211311
DATED            : March 22, 2011
INVENTOR(S)      : Sheena K. Aurora Page 1 of 2

It is certified that error appears in the above-identified patent and that said Letters Patent is hereby corrected as shown below:

On the first page, in field (56), under "OTHER PUBLICATIONS" in column 2, line 4, delete "Cephalagia" and insert -- Cephalalgia --, therefor.

On the first page, in field (56), under "OTHER PUBLICATIONS" in column 2, line 11, delete "Clincial" and insert -- Clinical --, therefor.

On page 2, in column 2, under "Other Publications", line 11, delete "partoid" and insert -- parotid --, therefor.

On page 2, in column 2, under "Other Publications", line 14, delete "nasaal" and insert -- nasal --, therefor.

On page 2, in column 2, under "Other Publications", line 39, delete "Nauny-Schmiedeberg's" and insert -- Naunyn-Schmiedeberg's --, therefor.

In column 1, line 42, delete "reflux" insert -- . --.

In column 7, line 48, delete "hemaglutinin" and insert -- hemagglutinin --, therefor.

In column 7, line 49, delete "nonhemaglutinin" and insert -- non hemagglutinin --, therefor.

In column 11, line 42, delete "intrasphincter" and insert -- intersphincteric --, therefor.

In column 11, line 46, delete "lid." and insert -- lid; --, therefor.

In column 11, line 51, delete "desired)." and insert -- desired); --, therefor.

In column 11, line 56, delete "sublimus" and insert -- sublimis --, therefor.

Signed and Sealed this
Seventh Day of February, 2012

David J. Kappos
*Director of the United States Patent and Trademark Office*

CERTIFICATE OF CORRECTION (continued)
U.S. Pat. No. 7,910,116 B2

In column 12, line 23, delete "It" and insert -- it --, therefor.

In column 12, line 38, delete "hyperhydrosis" and insert -- hyperhidrosis --, therefor.

In column 12, line 48, delete "Nauny-Schmiedeberg's" and insert -- Naunyn-Schmiedeberg's --, therefor.

In column 12, line 52, delete "Nauny-Schmiedeberg's" and insert -- Naunyn-Schmiedeberg's --, therefor.

In column 13, line 5, delete "hyperhydrosis" and insert -- hyperhidrosis --, therefor.

In column 14, line 22, delete "gangliocide" and insert -- ganglioside --, therefor.

In column 17, line 45, delete "cervogenic" and insert -- cervicogenic --, therefor.

In column 22, line 28, in claim 6, delete "cervogenic" and insert -- cervicogenic --, therefor.

In column 22, line 51, in claim 12, after "administration" insert -- of a --.

In column 22, line 59, in claim 12, after "a" delete "significant".